(12) United States Patent
Kido

(10) Patent No.: US 11,813,106 B2
(45) Date of Patent: Nov. 14, 2023

(54) IMAGE PROCESSING DEVICE, AND IMAGE PROCESSING METHOD UTILIZING TIME-SERIES COMPUTED TOMOGRAPHY (CT) IMAGES

(71) Applicant: NATIONAL UNIVERSITY CORPORATION EHIME UNIVERSITY, Ehime (JP)

(72) Inventor: Teruhito Kido, Ehime (JP)

(73) Assignee: NATIONAL UNIVERSITY CORPORATION EHIME UNIVERSITY, Ehime (JP)

( * ) Notice: Subject to any disclaimer, the term of this patent is extended or adjusted under 35 U.S.C. 154(b) by 556 days.

(21) Appl. No.: 17/058,694

(22) PCT Filed: May 28, 2019

(86) PCT No.: PCT/JP2019/021147
§ 371 (c)(1),
(2) Date: Nov. 25, 2020

(87) PCT Pub. No.: WO2019/230738
PCT Pub. Date: Dec. 5, 2019

(65) Prior Publication Data
US 2021/0196220 A1 Jul. 1, 2021

(30) Foreign Application Priority Data
May 29, 2018 (JP) .................................. 2018-102516

(51) Int. Cl.
*A61B 6/00* (2006.01)
*A61B 6/03* (2006.01)
*G06T 11/00* (2006.01)

(52) U.S. Cl.
CPC ............ *A61B 6/5217* (2013.01); *A61B 6/032* (2013.01); *G06T 11/008* (2013.01); *A61B 6/481* (2013.01);
(Continued)

(58) Field of Classification Search
CPC .. A61B 6/541; G06T 11/008; G06T 2211/412
See application file for complete search history.

(56) References Cited

U.S. PATENT DOCUMENTS 9,517,042 B2 * 12/2016 Hsieh ...................... A61B 6/504
10,102,623 B2 * 10/2018 Kido ..................... A61B 5/0275
(Continued)

FOREIGN PATENT DOCUMENTS

WO   2013/057982 A1   4/2013
WO   2016/009957 A1   1/2016

OTHER PUBLICATIONS

International Search Report (ISR) dated Aug. 20, 2019 filed in PCT/JP2019/021147.

*Primary Examiner* — Pakee Fang
(74) *Attorney, Agent, or Firm* — Rankin, Hill & Clark LLP

(57) ABSTRACT

An object of the present invention is to provide an analysis method capable of analyzing time-series images by a method simpler than ever. A computer program that is an application example of the present invention is a computer program for an image processing device including a storage unit that stores therein image data including time-series computed tomography (CT) images in a plurality of frames, of an organ of a subject captured after a contrast medium has been administered causes the image processing device to execute: a first step of determining a change-over-time of a CT value on the basis of image data including CT images in the plurality of frames; a second step of determining a predetermined slope that is a slope of the CT value with
(Continued)

respect to a predetermined time on the basis of a change-over-time of the CT value determined in the first step; and a third step of approximating a change-over-time of the CT value with a predetermined function on the basis of the predetermined slope determined in the second step.

5 Claims, 9 Drawing Sheets

(52) U.S. Cl.
CPC ............... *A61B 6/486* (2013.01); *A61B 6/503* (2013.01); *A61B 6/507* (2013.01); *G06T 2210/41* (2013.01); *G06T 2211/412* (2013.01)

(56) References Cited

U.S. PATENT DOCUMENTS

| | | | |
|---|---|---|---|
| 2011/0091087 A1* | 4/2011 | Ibarz | G06T 11/006 382/131 |
| 2014/0163403 A1 | 6/2014 | Lenox et al. | |
| 2014/0219539 A1 | 8/2014 | Yoshikawa | |
| 2017/0206652 A1 | 7/2017 | Kido | |
| 2018/0330502 A1* | 11/2018 | Ikeda | A61B 6/541 |
| 2019/0221012 A1* | 7/2019 | Fukuda | A61B 6/542 |
| 2019/0221013 A1* | 7/2019 | Fukuda | G06T 5/002 |
| 2021/0056683 A1* | 2/2021 | Nam | G06T 7/0012 |

\* cited by examiner

FIG. 7

(A) INPUT FUNCTION TABLE 700

| AT | MT | BL | SLOPE a | FUNCTIONS L AND F | ROI VALUE | MB |
|---|---|---|---|---|---|---|
| 23 | ... | 45 | ... | ... | ... | ... |

711, 712, 713, 714, 715, 717, 718

(B) OUTPUT FUNCTION TABLE 750

| SLICE NUMBER | PIXEL POSITION | SLOPE α | FUNCTION F |
|---|---|---|---|
| 1 | x1,y1 – x2,y2 | ... | ... |
| 1 | x3,y3 – x4,y4 | ... | ... |
| ... | ... | ... | ... |

761, 762, 763, 765

FIG. 8
(A)
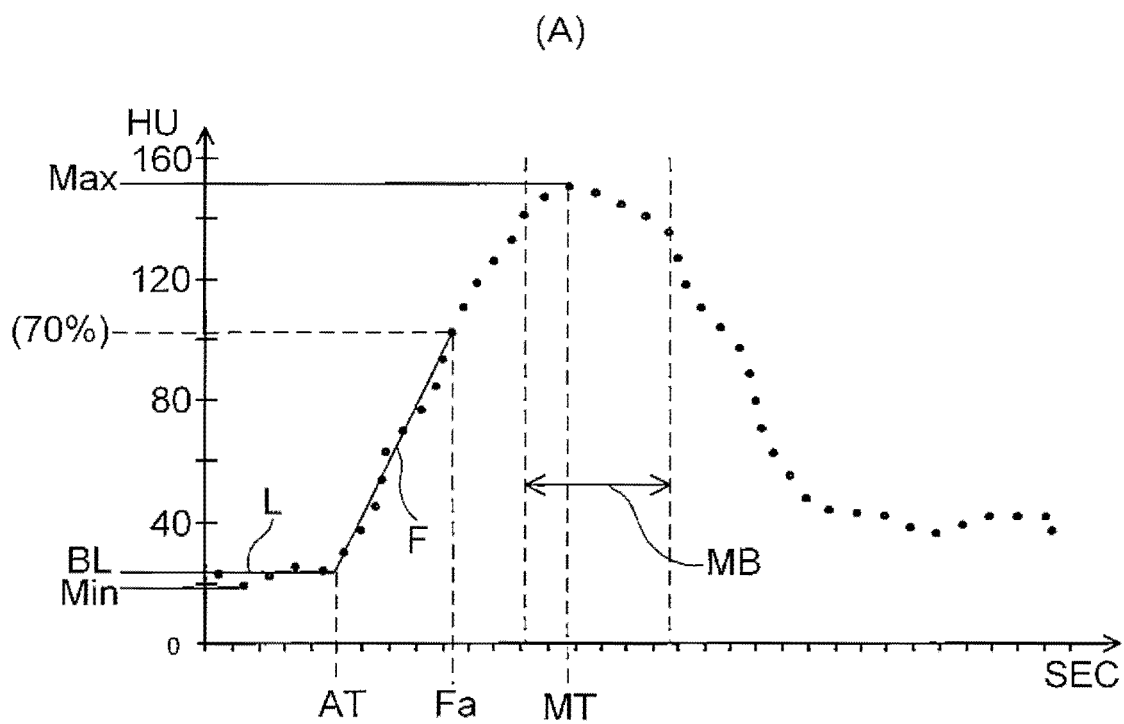
(B)
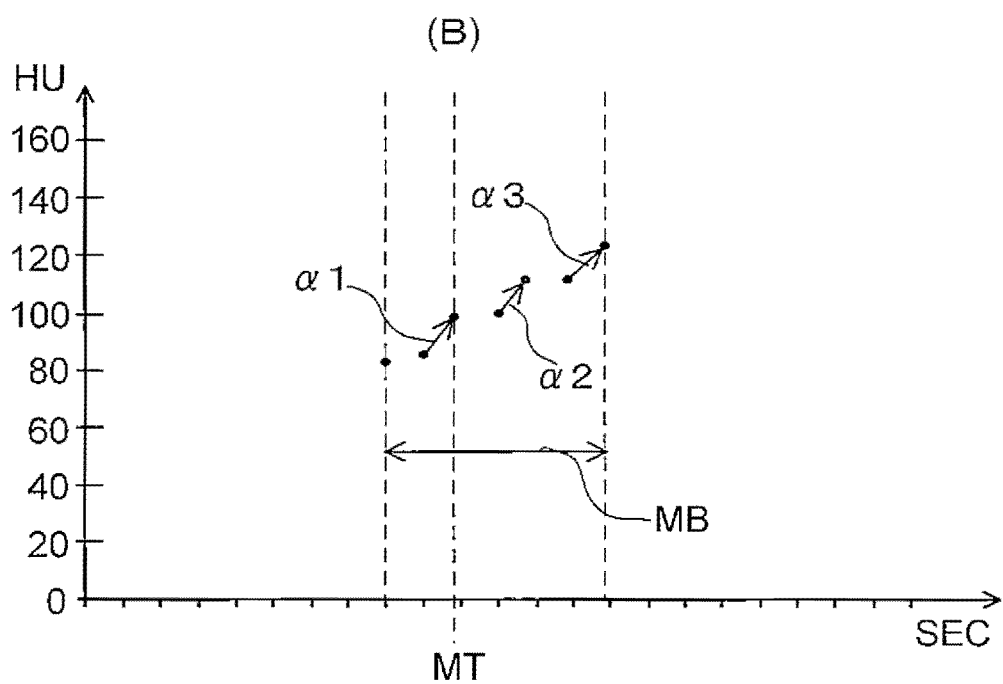

FIG. 9
(A)
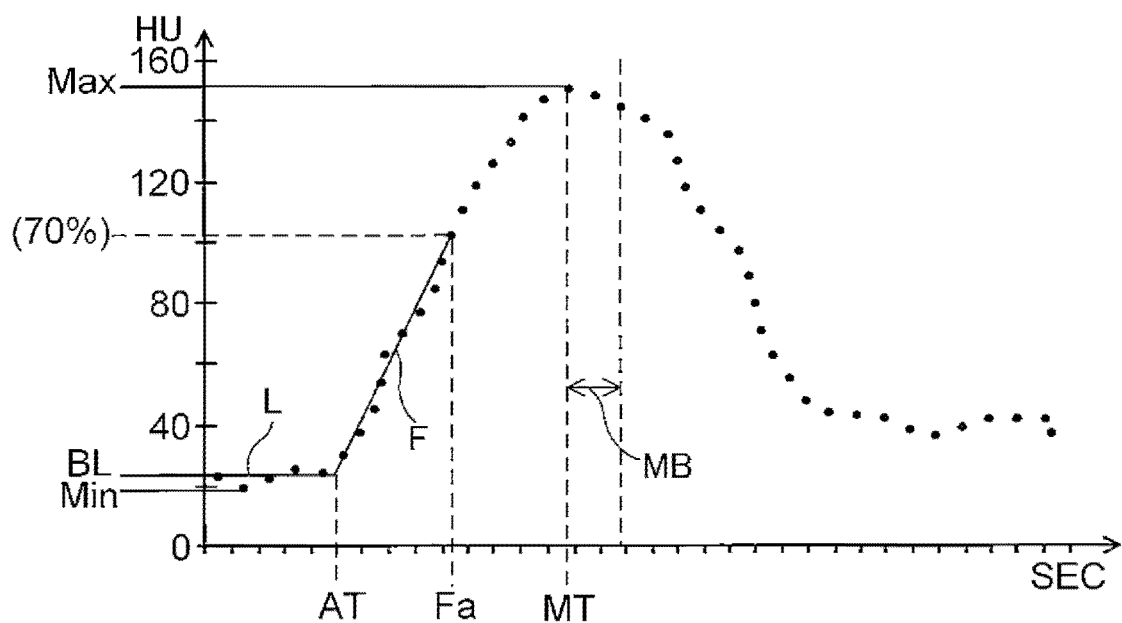
(B)
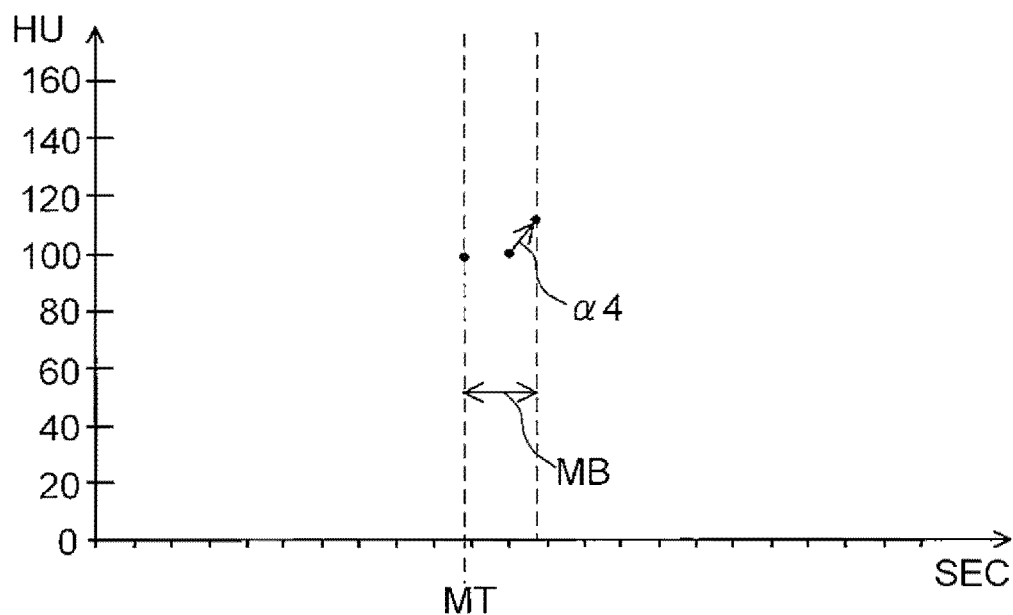

IMAGE PROCESSING DEVICE, AND IMAGE PROCESSING METHOD UTILIZING TIME-SERIES COMPUTED TOMOGRAPHY (CT) IMAGES

TECHNICAL FIELD

The present invention relates to an image processing technique, and particularly relates to a technique of analyzing time-series dynamic images.

BACKGROUND ART

A known method for analyzing a blood flow in the heart uses images of the heart of a subject captured after a contrast medium has been administered to the subject. Analysis methods for such myocardium perfusion include computed tomography perfusion (CTP) that is additionally conducted at the time of coronary CT inspection. The CTP is a method of assessing the state of myocardium perfusion, for example, by observing first pass of a contrast medium to a myocardium as a contrast effect. Assessment methods of CTP include a quantitative assessment on the myocardium perfusion through analysis on a time density curve (TDC) obtained by dynamic imaging that captures a gradually stained myocardium with a plurality of heartbeats.

Methods of quantitative assessment on the myocardium perfusion or the like through analysis on a TDC in this manner include a method of quantitative assessment on the myocardium perfusion, for example, after analyzing a CT image obtained by dynamic imaging, obtaining an input function and an output function, and, on the basis of the obtained input function and output function, calculating an arrival time (AT) indicating a time at which a contrast medium has arrived at a predetermined myocardium region and a base value, which is a CT value serving as a base of the pixel at an intra-organ pixel position (See, Patent Literature 1, for example).

CITATION LIST

Patent Literature

PATENT LITERATURE 1: International Publication No. 2016/009957

SUMMARY OF INVENTION

Problems to be Solved by Invention

However, the method described in Patent Literature 1 requires an analysis of CT images in the plurality of frames obtained by dynamic imaging with of at least 30 to 40 heartbeats, and the analysis processing is complicated, and it is hence desired an analysis method capable of analyzing time-series images by a simpler method. There has been a problem that the exposure to the subject increases because the CTP inspection for a time corresponding to at least 30 to 40 heartbeats is necessary. Therefore, it is also desired to accurately grasp the imaging timing, shorten the imaging time, and reduce the exposure to the subject.

In view of the above, an object of the present invention is to provide an analysis method capable of analyzing time-series images by a method simpler than ever. Another object of the present invention is to provide an objective and quantitative analysis method for analyzing time-series images, as well as for reducing the exposure to the subject compared with the conventional method.

Solution to Problems

The present invention has been made in order to solve at least a part of the above problems, and can be realized as application examples given below. It should be noted that parenthesized reference numerals, supplementary descriptions, and the like in this section indicate correspondence with the examples described later for a help of understanding of the present invention, and do not limit the present invention at all.

A computer program according to an application example 1 in the present invention is a computer program for an image processing device (100) including a storage unit (110) that stores therein image data including time-series computed tomography (CT) images in a plurality of frames, of an organ of a subject captured after a contrast medium has been administered causes the image processing device to execute: a first step (S350, S540) of determining a change-over-time of a CT value based on image data including CT images in the plurality of frames; a second step (S1100) of determining a predetermined slope that is a slope of the CT value with respect to a predetermined time based on a change-over-time of the CT value determined in the first step; and a third step (S1300) of approximating a change-over-time of the CT value with a predetermined function based on the predetermined slope determined in the second step.

A computer program according to an application example 2 of the present invention is the computer program of the application example 1, in which the predetermined slope is a slope of the CT value with respect to the predetermined time and is larger than a predetermined value.

A computer program according to an application example 3 of the present invention is the computer program of the application example 1 or 2, in which the storage unit stores first image data including CT images in a first predetermined number of frames, and second image data including CT images in a second predetermined number of frames that is smaller than the first predetermined number, and the computer program causes the image processing device to further execute a fourth step (S480) of determining a maximum timing that is a timing at which the CT value becomes a maximum value in a change-over-time of the CT value determined in the first step based on the first image data, and to execute the first step, the second step, and the third step based on the second image data including CT images in the second predetermined number of frames based on the maximum timing determined in the fourth step.

A computer program according to an application example 4 of the present invention is the computer program of the application example 3, the computer program causes the image processing device to execute the first step, the second step, and the third step based on the second image data including CT images in the second predetermined number of frames corresponding to one beat of the organ based on the maximum timing determined in the fourth step.

An image processing device according to the present invention includes: a storage unit (110) that stores therein image data including time-series computed tomography (CT) images in a plurality of frames, of an organ of a subject captured after a contrast medium has been administered; a first unit (123, 133) that determines a change-over-time of a CT value based on image data including CT images in the plurality of frames; a second unit (125, 137) that determines a predetermined slope that is a slope of the CT value with respect to a predetermined time based on a change-over-time of the CT value determined in the first unit; and a third unit (125, 137) that approximates a change-over-time of the CT value with a predetermined function based on the predetermined slope determined in the second unit.

An image processing method in the present invention is an image processing method that is executed by an image processing device (100) including a storage unit (110) that stores therein image data including time-series computed tomography (CT) images in a plurality of frames, of an organ of a subject captured after a contrast medium has been administered, in which the image processing device executes: a first step (S350, S540) of determining a change-over-time of a CT value based on image data including CT images in the plurality of frames; a second step (S1100) of determining a predetermined slope that is a slope of the CT value with respect to a predetermined time based on a change-over-time of the CT value determined in the first step; and a third step (S1300) of approximating a change-over-time of the CT value with a predetermined function based on the predetermined slope determined in the second step.

BRIEF DESCRIPTION OF DRAWINGS

FIG. 7(A) is a diagram illustrating an example of a data structure of an input function table 700 of an input function data storage unit 129, and FIG. 7(B) is a diagram illustrating an example of a data structure of an output function table 750 of an output function data storage unit 139.

FIG. 8(A) is a diagram illustrating an example of a first TDC of the aorta in the first example, and FIG. 8(B) is a diagram illustrating an example of a second TDC of the intramyocardial coronary artery in the first example.

FIG. 9(A) is a diagram illustrating an example of a first TDC of the aorta in the second example, and FIG. 9(B) is a diagram illustrating an example of a second TDC of the intramyocardial coronary artery in the second example.

DESCRIPTION OF EMBODIMENTS

Examples to which the present invention is applied will be described below with reference to the drawings. Embodiments of the present invention are not limited to the following examples, and various examples can be adopted as long as they fall within the technical scope of the present invention.

First Example

<Configuration of Image Processing Device 100>

Figure 1:
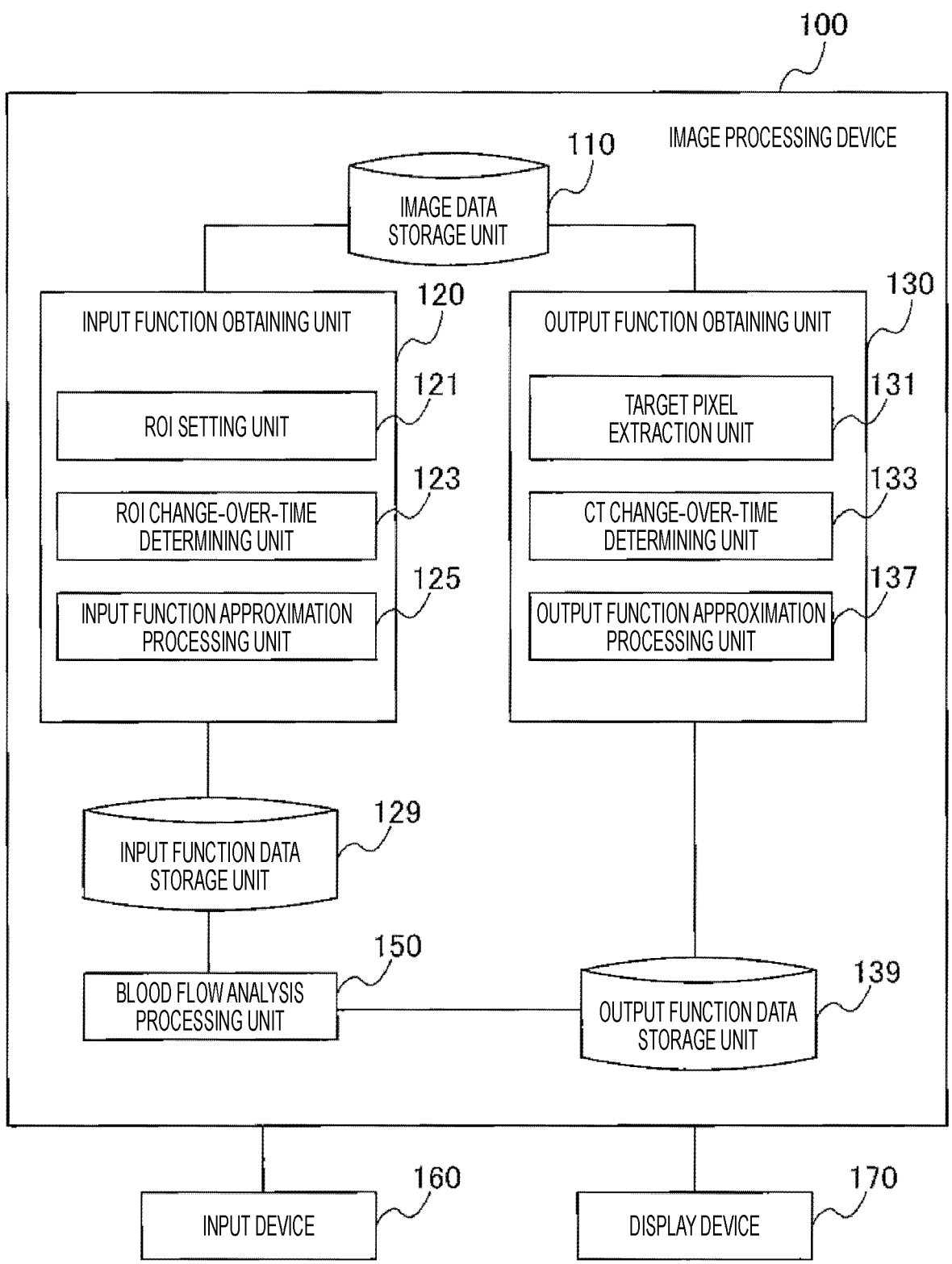
FIG. 1 is a diagram illustrating an overall configuration of an image processing device 100 in a first example, which is an example of the present invention.

With reference to FIG. 1, the configuration of an image processing device 100 of the present example will be described first. FIG. 1 is a diagram illustrating the overall configuration of the image processing device 100. The image processing device 100 includes a general-purpose computer system, for example. Components or functions in the image processing device 100 that are described below are each implemented by executing a computer program that is stored in a computer-readable recording medium or the like. The image processing device 100 of the present example includes an image data storage unit 110, an input function obtaining unit 120, an input function data storage unit 129, an output function obtaining unit 130, an output function data storage unit 139, and a blood flow analysis processing unit 150. An input device 160 and a display device 170 are connected to the image processing device 100.

The image processing device 100 is a device that uses CT images of an organ of a subject captured after a contrast medium has been administered, to perform quantitative analysis on a blood flow rate in the organ. In the present embodiment, the image processing device 100 performs pixel-based analysis on a plurality of CT frame images of the same phase of the heart of the subject captured in synchronization with electrocardiogram, to determine an input function and an output function or the like that are used for calculating a quantitative value of a myocardium blood flow in the heart and the vicinity of the heart. In the present embodiment, the image processing device 100 estimates the myocardium blood flow rate on the basis of a change in a pixel value of the CT image due to the contrast medium administrated in the vein. For example, when the pixel value of the CT image sharply changes in response to the arrival of the contrast medium at a target portion, the base value is determined as a pixel value before the arrival and the arrival time (AT) is determined as a time at which the change in the pixel value starts. While various contrast media can be used, in the present example, iopromide, for example, is used as the contrast medium.

The image data storage unit 110, which is a general memory in a computer system, stores, in the present embodiment, image data of CT images of the heart and the vicinity of the heart obtained by imaging the heart. The CT image is a CT image including nine-series CT images in a plurality of frames, of the organ of the subject captured after the contrast medium has been administered, and is a three-dimensional image (three-dimensional voxel data) including a plurality of slice images (short-axis images), whose details will be described later.

The input function obtaining unit 120 obtains an input function or the like on the basis of image data stored in the image data storage unit 110. The input function relates to change in a pixel value of the CT image (hereinafter, referred to as a CT value) due to the contrast medium flowing into the organ of the subject. The input function obtaining unit 120 has an ROI setting unit 121, an ROI change-over-time determining unit 123, and an input function approximation processing unit 125, which will be described below. The input function data storage unit 129 stores, as an input function table 700 described later, data related to the input function or the like obtained by the input function obtaining unit 120.

The ROI setting unit 121 sets a region of interest (ROI), which is a region for determining an input function in the CT image, according to an operation through the input device 160 by an analyst such as a physician. Specifically, the ROI setting unit 121 reads out image data from the image data storage unit 110, displays the frame image of a slice including a target region on the display device 170, and sets the ROI in the image displayed on the display device 170, in accordance with an input from the analyst through the input device 3. The position of the ROI is the same among all the frames corresponding to the same slice.

The ROI change-over-time determining unit 123 determines the change-over-time in the CT value in the ROI, on the basis of the image data on the time-series CT images in a plurality of frames. Specifically, the ROI change-over-time determining unit 123 generates a TDC of the ROI value based on the CT value in the ROI, as the change-over-time in the CT value in a predetermined region in the CT image. The ROI value is a value (statistical value) as a result of processing the CT values in the ROI with a statistical algorithm, and can be any of a mean value, a mode value, a median value, a maximum value, a minimum value and the like.

On the basis of the TDC generated by the ROI change-over-time determining unit 123, the input function approximation processing unit 125 determines MT, which is a time at which the CT value in the ROI becomes the maximum value Max, AT, which is a time at which a contrast medium has arrived at a region where the ROI is set, MB, which is an imaging section of an imaging period for obtaining the second TDC described later, an input function, and the like. In the TDC generated by the ROI change-over-time determining unit 123, the input function approximation processing unit 125 executes smoothing processing so that the TDC has a smooth curve, and then determines an input function or the like. The input function approximation processing unit 125 also determines an upper limit frame Fa, which is a predetermined frame after a sharp rise in the CT value, and a base value BL, which will be described later.

On the basis of image data stored in the image data storage unit 110, the output function obtaining unit 130 obtains an output function or the like related to a change in the CT value of the CT image due to the contrast medium flowing into the blood vessel of the organ of the subject. The output function obtaining unit 130 obtains the output function for pixels instead of ROIs, and includes a target pixel extraction unit 131, a CT change-over-time determining unit 133, and an output function approximation processing unit 137. The output function data storage unit 139 stores, as an output function table 750 described later, data related to the output function obtained by the output function obtaining unit 130.

The target pixel extraction unit 131 extracts a pixel for which the output function is obtained, and determines the position of the pixel on the frame image. Specifically, the target pixel extraction unit 131 selects pixels with the CT value within a predetermined range (for example, 50 to 160) for each slice, in all the time-series CT images in a plurality of frames as extraction processing. In this extraction processing, in a case where the region of the target pixel includes a small non-target region, the region is regarded as a processing deficit, and processing of converting the pixel into the target pixel can be executed in accordance with the size of the non-target region (for example, whether the number of pixels is a predetermined number or less). When there is an isolated target pixel outside the region of the target pixel, processing to set the region as the non-target region can be executed in accordance with the size of the isolated target region (for example, whether the number of pixels is a predetermined number or less). The target pixel extraction unit 131 determines a position of the pixel thus extracted for each slice, as a position of the target pixel (an intra-organ pixel position) for which the output function is calculated.

The CT change-over-time determining unit 133 determines the change-over-time in the CT value of the pixel at the target pixel position (intra-organ pixel position) on the basis of the image data on the time-series CT images in a plurality of frames. Specifically, the CT change-over-time determining unit 133 generates the TDC representing the change-over-time in the CT value at the target pixel position for each slice.

The output function approximation processing unit 137 determines an output function or the like on the basis of the TDC generated by the CT change-over-time determining unit 133. Specifically, the output function approximation processing unit 137 calculates the value of the slope between the CT values on the basis of the TDC that is the change-over-time determined by the CT change-over-time determining unit 133, and determines the output function on the basis of the slope of a predetermined value or more of the calculated slope values.

The blood flow analysis processing unit 150 performs the quantitative analysis for the blood flow rate on the basis of the input function and the output function. Specifically, the blood flow analysis processing unit 150 executes predetermined analysis processing by referring to the input function table 700 of the input function data storage unit 129 and the output function table 750 of the output function data storage unit 139. Examples of the blood flow quantitative analysis method include a Patlak plot and deconvolution, to determine the myocardial blood flow (MBF), the myocardial blood volume (MBV), the mean transit time (MTT), and the like. Specifically, the predetermined analysis processing is executed on the basis of a slope α of a function F of the input function table 700 described later or the data of the function F, and a slope α of the output function table 750 or the data of the function F. The result of the quantitative analysis performed by the blood flow analysis processing unit 150 is displayed on the display device 170. At this time, for example, the result of the quantitative analysis is displayed side by side with the CT image or is overlapped on the CT image. Hence, the coronary stenosis and the myocardium ischemia can be concurrently assessed through comparison between two images, in cases such as myocardium infraction or angina. For example, in the case where the determined MBF is lower than the normal MBF through comparison between the determined MBF and the normal MBF, it can be judged as an ischemic state, and eventually, the coronary stenosis and the myocardium ischemia can be assessed in cases such as myocardium infraction or angina in the myocardium coronary.

<Configuration of CT Image Data>

Figure 2:
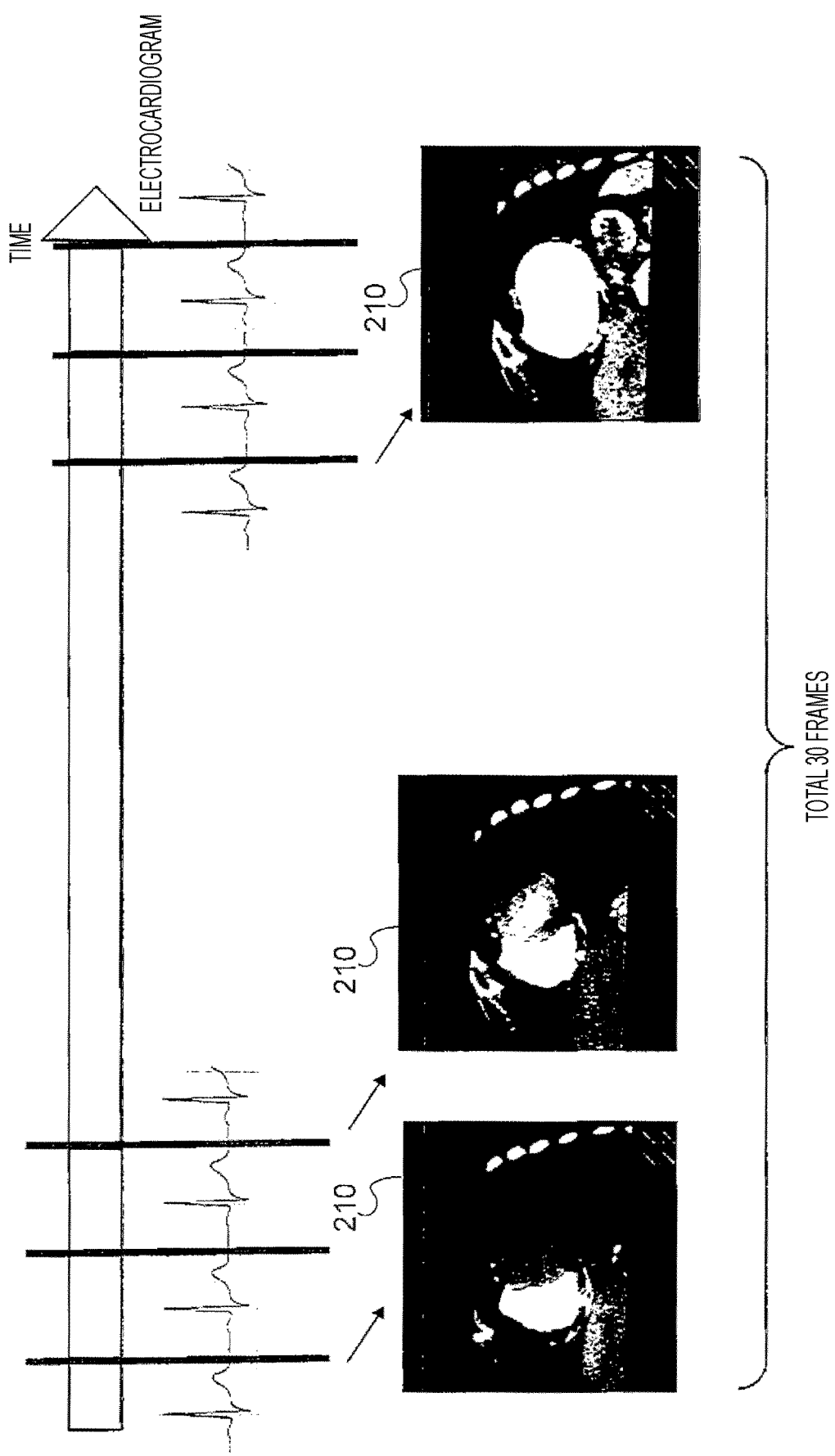
FIG. 2 is diagram illustrating an example of a CT image.

The CT image stored in the image data storage unit 110 will be described with reference to FIG. 2. FIG. 2 is diagram illustrating an example of the CT image. The CT image shown in FIG. 2 is a predetermined number of (for example, 30) frame images 210 of the heart corresponding to the same phase of the heartbeat, captured in synchronization with the electrocardiogram. A single frame includes a plurality of slice images, and data on a single frame include three-dimensional image data. FIG. 2 illustrates an example of frame images obtained with a single slice. The CT image may be started to be captured immediately after the contrast medium is administered to the subject, and the CT image may include 1st to 30th frames in the captured order.

<Content of Input Function Obtaining Processing>

Figure 3:
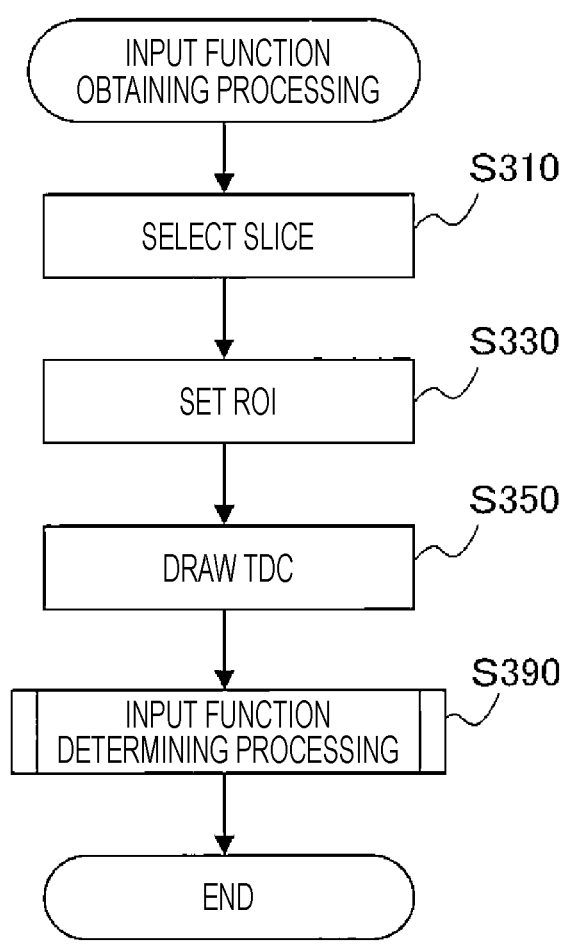
FIG. 3 is a flowchart illustrating input function obtaining processing.
Figure 4:
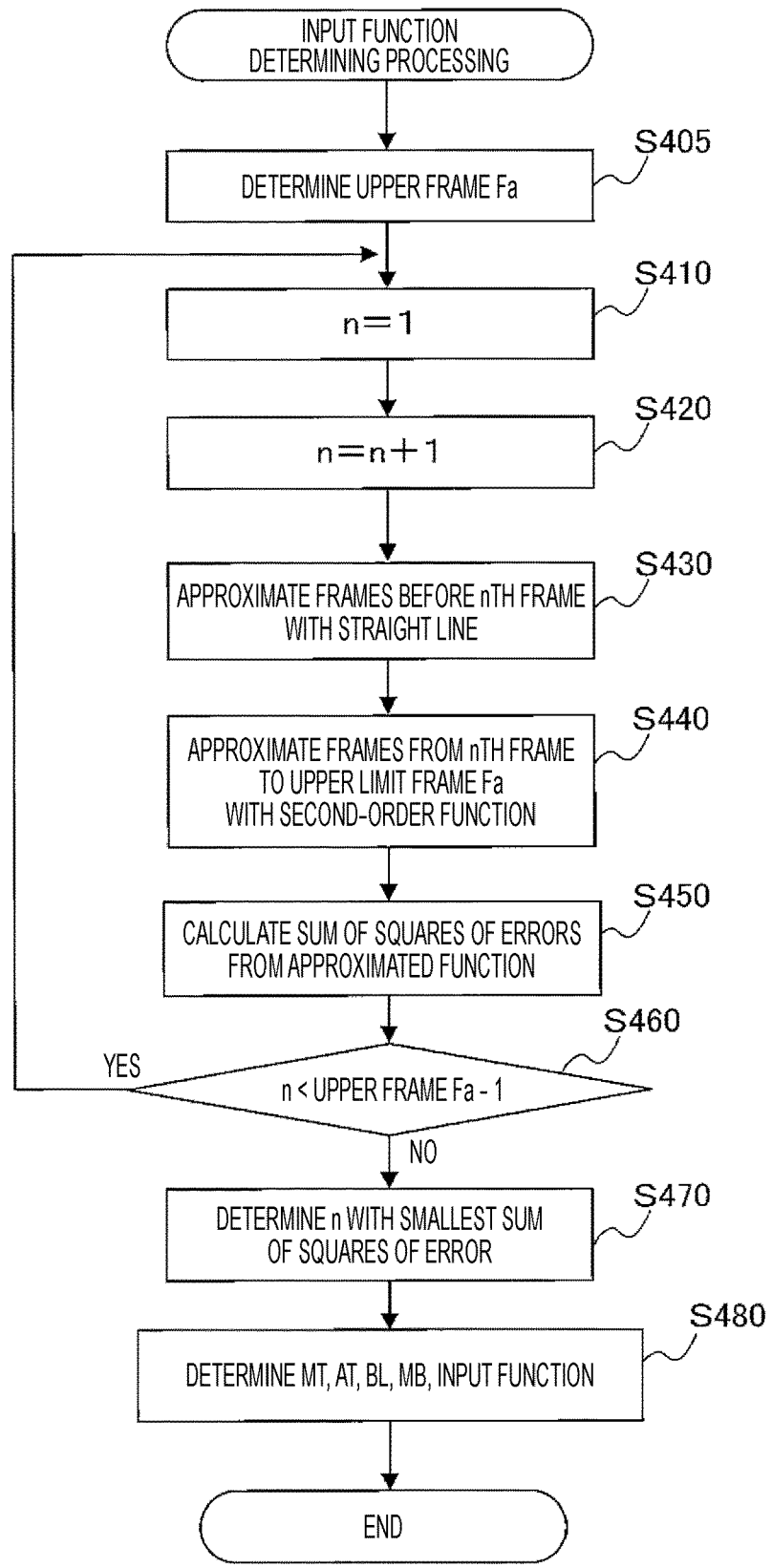
FIG. 4 is a flowchart illustrating input function determining processing.

Next, the input function obtaining processing executed by the input function obtaining unit 120 will be described with reference to FIGS. 3 and 4. FIG. 3 is a flowchart illustrating the input function obtaining processing. FIG. 4 is a flowchart illustrating the input function determining processing.

As shown in FIG. 3, in the input function obtaining processing, first, the ROI setting unit 120, along the selection process by the analyst, reads out image data of the frame image of a slice image including a specific region from the image data storage unit 110 (S310), and sets an ROI in accordance with an operation of the analyst, while the display device 5 is displaying the frame image, in the slice image thus selected, in which the specific region is clearly visible (S330). Next, the ROI change-over-time determining unit 123 calculates the ROI values for all the frame images for which the ROI is set, and draws the TOC based on the ROI values (S350). Then, the input function approximation processing unit 125 executes the input function determining processing to be described later (S390).

As shown in FIG. 4, in the input function determining processing, first, the input function approximation processing unit 125 determines on the basis of the TDC generated by the ROI change-over-time determining unit 123 the upper limit frame Fa defining a range of frames for which the input function is obtained (S405), sets a variable n indicating the frame number to 1 (S410), and increments n by 1 (S420). Next, the input function approximation processing unit 125 approximates the ROI values in frames before the nth frame to a single straight line L (S430), and approximates the ROI values in frames at and after the nth frame and at and before the upper limit frame Fa to the second-order function F (S440). Next, the input function approximation processing unit 125 calculates least square errors between the straight line L and the ROI values in the frames before the nth frame, calculates the least square errors between the second-order function F and the ROI values in the frames at and after the nth frame and at and before the upper limit frame Fa to the second-order function F, and obtains the sum of the least square errors (S450). Then, the input function approximation processing unit 125 repeats the processing from steps S410 to S450, until n reaches the upper limit frame Fa−1 (YES in S460), and calculates all the sums of the least square errors from n=2 to the upper limit frame Fa−1. When all the sums of the least square errors from n=2 to the upper limit frame Fa−1 are obtained (NO in S460), the input function approximation processing unit 125 determines n with the smallest sum of the least square errors (S470). Then, the input function approximation processing unit 125 defines an MT as the frame in which the ROI value in the TDC becomes the maximum value Max, an AT as the frame at the intersection between the straight line L and the second-order function F corresponding to n thus determined in step S470, an BL as the ROI value (the height of the straight line L (Y-intercept)) in the frame defined as AT, and an imaging section MB as the period corresponding to the predetermined heartbeat before and after the MT, and determines a slope of the input function and the input function.

<Content of Output Function Obtaining Processing>

Figure 5:
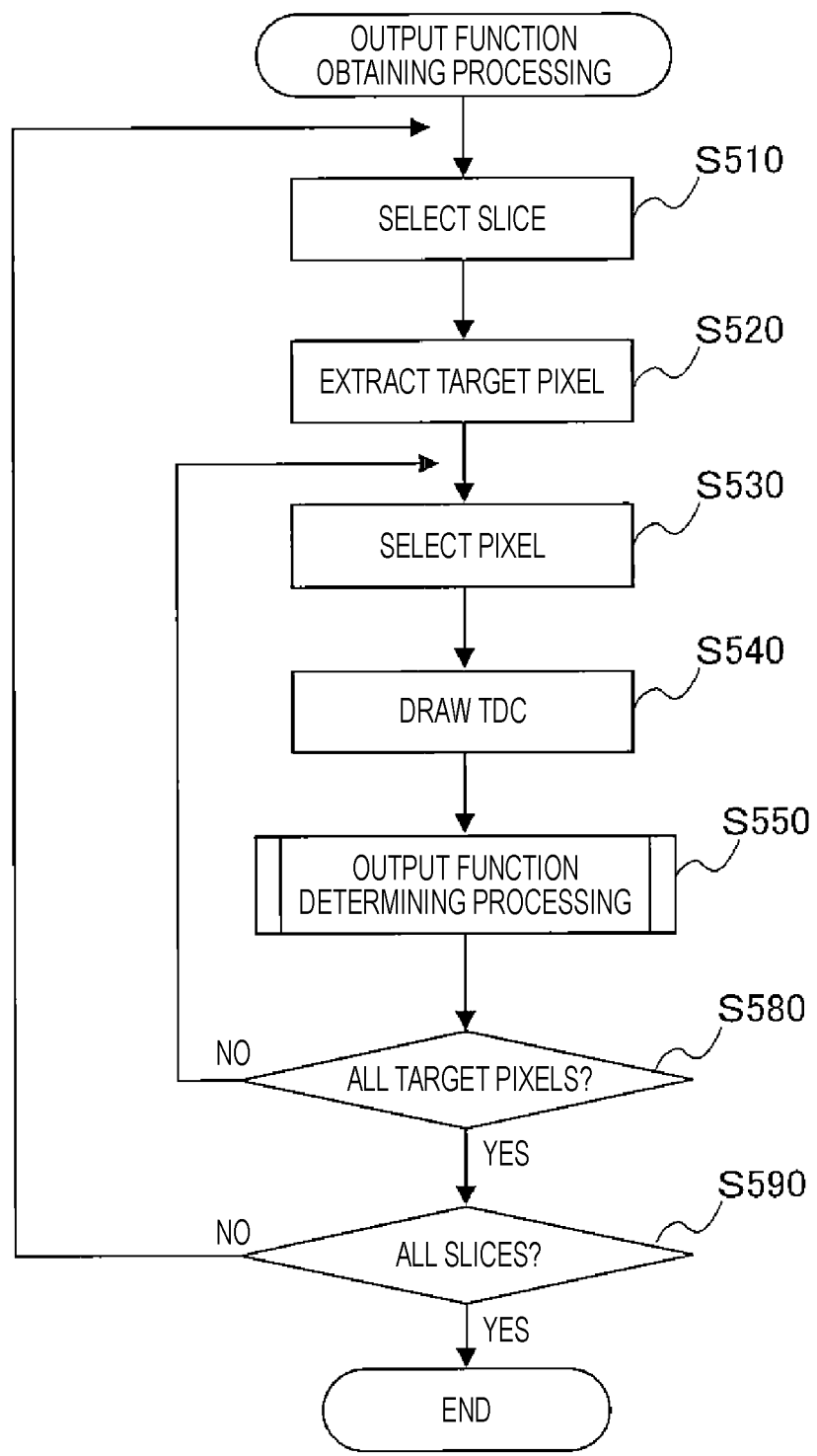
FIG. 5 is a flowchart illustrating output function obtaining processing.
Figure 6:
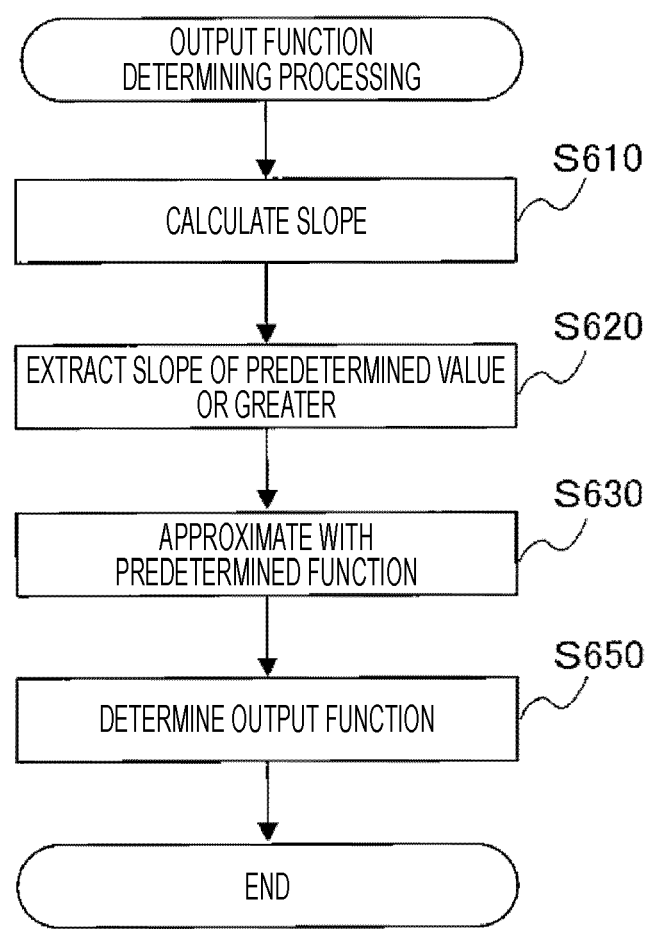
FIG. 6 is a flowchart illustrating output function determining processing.

The output function obtaining processing executed by the output function obtaining unit 130 will be described with reference to FIGS. 5 and 6. FIG. 5 is a flowchart illustrating the output function obtaining processing. FIG. 6 is a flowchart illustrating the output function determining processing.

As shown in FIG. 5, in the output function obtaining processing, first, the target pixel extraction unit 131 selects a single slice image, and reads image data on frame images corresponding to the slice from the image data storage unit 110 (S510), regards, from among all the pixels in the slice selected, pixels, for which the CT values in all the frame images satisfy the condition described above, as the pixel in a specific region, and extracts the pixels as the target pixels (S520), and selects one of the target pixels extracted (S530). Next, the CT change-over-time determining unit 133 draws the TDC for the pixel selected by the target pixel extraction unit 131 (S540). Next, the output function approximation processing unit 137 executes on the basis of the CT value the output function determining processing to be described later, and determines an output function or the like (S550). Then, the output function obtaining unit 130 executes the processing from steps S530 to S550 on all the target pixels (S580), and executes the processing from steps S510 to S580 on all the slices (S590).

As shown in FIG. 6, in the output function determining processing, first, the output function approximation processing unit 137 calculates the slope α between plots in the TDC generated by the CT change-over-time determining unit 133 (S610), and extracts only the slope that becomes equal to or greater than a predetermined value (for example, 0.2 or more) in the calculated slope (S620). Then, the output function approximation processing unit 137 performs approximation with a predetermined function on the basis of the extracted slope α (S630), and determines the output function (S650).

<Configuration of Input Function Table 700 and Output Function Table 750>

The data structures of the input function table 700 stored in the input function data storage unit 129 and the output function table 750 stored in the output function data storage unit 139 will be described with reference to FIGS. 7(A) and 7(B). FIGS. 7(A) and 7(B) are diagram illustrating an example of the data structure of the input function table 700 and the output function table 750, and FIG. 7(A) is a diagram illustrating an example of the data structure of the input function table 700 of the input function data storage unit 129, and FIG. 7(B) is a diagram illustrating an example of the data structure of the output function table 750 of the output function data storage unit 139.

As illustrated in FIG. 7(A), the input function table 700 includes the AT 711, the MT 712, the BL 713, the slope a 714 of the function F, the functions L and the F 715, the ROI value 717, and the MB 718 as data items. The functions L and the F 715 are an expression of the straight line L and an expression of the second-order function F as a result of approximating by the input function approximation processing unit 125 for a frame n=1 to the upper limit frame Fa, and the ROI value 717 is the ROI value of each of frames for forming the TDC. The blood flow analysis processing unit 150 may use the input function in the input function table 700 for the blood flow analysis, with the ROI value 717 or the functions L and F 715 corrected in such a manner that the AT 711 and the BL 715 are set to be at the origin.

As illustrated in FIG. 7(B), the output function table 750 includes a slice number 761, the pixel position 762, the slope α 763, and the function F 765 as data items. The pixel position 762 is data indicating the positions of two CT values that are the bases for calculating the slope α 763, and the function F 765 is an expression of the function F that is an approximate expression calculated from the slope α 763.

<Content of Image Processing for CT Images of Heart>

Next, the image processing of the CT image of the heart in the present example will be specifically described. The image processing for the TDC based on the CT image of the heart in the present example has a flow in which the imaging using a test injection method using a contrast medium diluted to a predetermined concentration with physiological saline example, a contrast medium diluted fourfold with physiological saline) is performed on the heart, and then the imaging using an undiluted contrast medium is performed. Specifically, first, a first CT image, which is a CT image of the heart including the aorta of the subject, is captured by performing imaging by the test injection method. Then, on the basis of the first CT image, the image processing device 100 executes the input function obtaining processing as described above, and hence the first TDC of the aorta is generated, and the MB, the input function, and the like are determined. Next, a second CT image, which is a CT image of the heart including the aorta and intramyocardial coronary artery of the subject, is captured by performing imaging using an undiluted contrast medium at the MB determined on the basis of the first TDC. Then, on the basis of the second CT image, the image processing device 100 executes the output function obtaining processing as described above, and hence the second TDC of the intramyocardial coronary artery is generated, and the output function and the like are determined. The quantitative analysis on the blood flow rate of the intramyocardial coronary artery is executed by the image processing device 100 on the basis of the thus determined an input function, an output function, and the like.

An outline of image processing for the first TDC and the second TDC will now be described with reference to FIGS. 8(A) and 8(B). FIGS. 8(A) and 8(B) are diagrams illustrating an example of the TDC in the present example, FIG. 8(A) is a diagram illustrating an example of the first TDC of the aorta in the present example, and FIG. 8(B) is a diagram illustrating an example of the second TDC of the intramyocardial coronary artery in the present example. FIG. 8(A) presents a case where the ROI is set in the aorta in the first CT image in the vicinity of the aorta of the heart, and FIG. 8(B) presents a case where the target pixel is set to a predetermined CT value (50 to 150 HU in the present example).

As illustrated in FIG. 8(A), first, the first TDC of the aorta is generated by the image processing of the image processing device 100 on the basis of the first CT image of the heart obtained by the test injection method, and the MB and the like are determined on the basis of the first TDC. Specifically, the ROI change-over-time determining unit 123 of the input function obtaining unit 120 first applies the ROI set by the ROI setting unit 121 to other frame images 210 corresponding to the same slice, and determines the ROI value that represents the ROI on the basis of the CT value of the pixels in the ROI for each frame image. Next, the ROI change-over-time determining unit 123 generates the first TDC by plotting the ROI values determined for all the frames corresponding to the same slice. Next, the ROI change-over-time determining unit 123 detects the maximum value Max of the CT value on the first TDC or a first peak value after a large rise of the curve (sharp rise in the CT value). The ROI change-over-time determining unit 123 adopts a value of a certain percentage (for example, 70%, 80%, 90%, or the like can be set, and 70% is adopted in the present example) between a minimum value Min of the ROI values on the TDC and the maximum value Max or the peak value.

Then, the input function approximation processing unit 125 sets, to the upper limit frame Fa, a frame that is before a frame from which the maximum value Max or the peak is detected and is of a certain percentage determined by the ROI change-over-time determining unit 123 as described above. Next, the input function approximation processing unit 125 obtains a formula corresponding to the straight line L with a linear approximation method using a least squares method and the like on ROI values before the nth frame Fn (n being any number between 2 and the upper limit frame Fa−1), and obtains a formula corresponding to a quadratic function F by approximating to a second-order function with the least squares method and the like applied to the ROI values corresponding to frames front the nth frame Fn to the upper limit frame Fa. Next, the input function approximation processing unit 125 calculates a sum of squares of errors between the straight line L and the ROI values before the nth frame Fn, and calculates a sum (residual sum of squares) of squares of errors between the second-order function F and the ROI values at and after the nth frame Fn. Then, the input function approximation processing unit 25 executes the processing described above for all the n variables, and determines n with the smallest sum of squares of the errors, determines as an approximated function each of the straight line L and the second-order function F with the smallest error n, and determines the slope a of the approximated function. Here, the frame where the ROI value becomes the maximum value Max is determined as the MT, the frame at the intersection (boundary) between the straight line L and the second-order function F is determined as the AT, the ROI value of the frame at the intersection (boundary) between the straight line L and the second-order function F is determined as the BL, and the section corresponding to three heartbeats before and after the MT is determined as the MB. Thus, the input function approximation processing unit 125 determines the MT, the AT, the BL, the MB, the slope a, and the input function of the region of the aorta on the basis of the first TDC. In the determination of the BL described above, for example, the height (Y-intercept) of the straight line L may be used as the BL instead of the ROI value.

Here, the MB, which is an imaging section serving as timing for performing imaging for obtaining the second CT image, will be described. In general, since the contrast medium flows into the intramyocardial coronary artery after the contrast medium flows into the aorta, a CT image for the intramyocardial coronary artery into which the contrast medium flows can be acquired by acquiring a CT image by imaging in a section corresponding to a predetermined number of heartbeats before and after the MT. In the second CT image in particular, in order to obtain the CT value of the intramyocardial coronary artery at the frame when the contrast medium surely flows into the intramyocardial coronary artery, the imaging section MB in the present example is set to the section corresponding to one heartbeat before the MT and two heartbeats after the MT.

As illustrated in FIG. 8(B), the second TDC of the intramyocardial coronary artery is generated by image processing of the image processing device 100 based on the second CT image obtained by imaging at the MB, and an output function or the like is determined on the basis of the second TDC. Since blood mainly flows into the intramyocardial coronary artery in the diastolic period of the heart accompanied by the heartbeat, a change occurs in the CT value between the diastolic period and the non-diastolic period of the heart, and the second TDC becomes a plot in which a step is formed. Therefore, when the output function is determined on the basis of the second TDC, it is possible to determine an output function with high accuracy by approximating the output function on the basis of a value of a slope equal to or greater than a predetermined value. Specifically, the values of the slopes between the plots in the second TDC based on the imaging in the imaging section MB are calculated, the values of slopes $\alpha1$ to $\alpha3$ that are equal to or greater than a predetermined value are extracted from all the slope values, and the output function is determined by the output function determining processing based on the slopes α1 to α3.

Here, as described above, the aspect of the change of the value of the slope during one heartbeat in the second TDC along the relationship between the diastolic period and the non-diastolic period of the heart is an aspect in which a first half is the value of a small slope and a second half is the value of a large slope. The value of the slope used in the output function determining processing is assumed to be the slopes α1 to α3, which are the values of the large slope in the second half of one heartbeat. In other words, the output function determining processing is processing using the value of the slope of the second half of the slope in one heartbeat in the second TDC. When the output function is determined, the output function may be determined by using the mean value of the slopes α1 to α3, or the output function may be determined by various determining methods after each approximate expression of the slopes α1 to α3 is determined.

Second Example

The image processing of the CT image of the heart in the second example will next be specifically described with reference to FIGS. 9(A) and 9(B). FIGS. 9(A) and 9(B) are diagrams illustrating an example of the TDC in the second example, FIG. 9(A) is a diagram illustrating an example of the first TDC of the aorta in the second example, and FIG. 9(B) is a diagram illustrating an example of the second TDC of the intramyocardial coronary artery in the second example. It should be noted that since the configuration of the image processing device 100 in the second example is the same as that in the first example, and the flows of the input function obtaining processing and the output function obtaining processing in the second example is substantially the same as those in the first example, the descriptions of <Configuration of Image Processing Device 100>, <Content of Input Function Obtaining Processing>, <Content of Output Function Obtaining Processing>, and the like will be omitted.

As illustrated in FIG. 9, also the image processing of the CT image of the heart in the second example has, similarly to the first example described above, a flow in which the imaging using the test injection method is performed on the heart, and then the imaging using an undiluted contrast medium is performed. However, unlike the first example described above, the MB determined on the basis of the first TDC in the second example is a section corresponding to one heartbeat, and the second TDC is also generated corresponding to one heartbeat. Then, a slope α4 in the second TDC based on the imaging in the imaging section MB is extracted, and the output function is determined by the output function determining processing based on the slope α4. It should be noted that the MB, which is an imaging section in the second example, is a section that corresponds to one heart beat after the MT in order to obtain the CT value of the intramyocardial coronary artery in the frame when the contrast medium flows surely into the intramyocardial coronary artery.

<Characteristics of First Example and Second Example>

As described above, according to the image processing device 100 of the first and second examples, it is possible to determine in S540 the second TDC, which is a change-over-time of the CT value, on the basis of image data including time-series second CT images in a plurality of frames captured at the MB, which is an imaging section, to extract in S620 the predetermined slopes α1 to α3 and α4, which are slopes of the CT values between the plots in the second TDC, and to perform approximation in S630 with a predetermined function on the basis of the predetermined slopes α1 to α3 and α4. In particular, processing in which the slopes α1 to α3 and α4 larger than the predetermined value are extracted can be performed for a plurality of slopes calculated in the MB, which is an imaging section. Therefore, when used for image processing for a CT image of the intramyocardial coronary artery, for example, the image processing device 100 of the first and second examples can eliminate data of the non-diastolic period of the heart where myocardial blood is not originally flowing, and can perform accurate image processing based on data of the diastolic period, and eventually, the accurate quantitative analysis of the blood flow. Since the analysis can be performed by a simpler method than that for the conventional image processing, the load on the image processing device 100 due to the image processing can also be reduced.

According to the image processing device 100 of the first and second examples described above, the image data storage unit 110 stores the first image data including the first CT image in the first predetermined number of frames and the second image data including the second CT image in the second predetermined number, which is smaller than the first predetermined number, of frames, and, on the basis of the MT determined from the first CT image obtained by the imaging by the test injection method using the diluted contrast medium, the image processing device 100 can determine the MB, which is the imaging section corresponding to the predetermined heartbeat, perform imaging using the undiluted contrast medium in the MB, and, on the basis of the obtained second CT image, execute image processing. Therefore, compared to the case of a CTP inspection for a period corresponding to 20 to 30 heartbeats as conventionally, it is possible to perform image processing with a CT image by the imaging in the MB, which is an imaging section that is a period corresponding to a smaller number of heartbeats, and hence it is possible to reduce the exposure of the subject and perform image processing based on the simple inspection.

Furthermore, the image processing device 100 of the second example described above can perform image processing on the basis of the second CT image and the second TDC in the number of frames corresponding to one beat based on the MB, which is an imaging section. Therefore, compared to the case of a CTP inspection for a period corresponding to 20 to 30 heartbeats as conventionally, it is possible to perform image processing with a CT image by the UP inspection in the imaging section MB, which is a period corresponding to a smaller number of heartbeats, and hence it is possible to reduce the exposure of the subject and perform image processing based on the simple inspection.

Other Examples

In the above-described examples, the section corresponding to three heartbeats or one heartbeat before and after the MT based on the first CT image is defined as the MB, which is an imaging section, but the present invention is not limited thereto, and the MB may be set as follows. For example, a period corresponding to two heartbeats or 4 to 10 heartbeats before and after the MT may be set to the MB, which is an imaging section. Even with imaging based on the MB and the imaging timing, it is possible to reduce the exposure of the subject and perform image processing based on the simple inspection.

In the above example, in the output function determining processing illustrated in FIG. 6, only the slope having a calculated slope of 0.2 or more is extracted, but the present invention is not limited to this, and a numerical value other than 0.2 may be used as a threshold value. For example, a numerical value based on a statistical value calculated from the results of a plurality of times of imaging may be used as a threshold value. With such a threshold value, it is possible to perform more accurate image processing, and eventually, the accurate quantitative analysis of the blood flow.

In the above example, in the output function determining processing illustrated in FIG. 6, only the slope having a calculated slope of 0.2 or more is extracted, that is, only the value of the slope (the second half of a slope in one heartbeat) in the diastolic period of the heart is extracted, but the present invention is not limited to this, and the output function may be determined on the basis of a change in the CT value in the non-diastolic period of the heart. Specifically, for example, it may be processing of extracting a slope that is less than 0.2 in the second TDC, and determining an output function by a difference method or the like based on a difference between changes in CT values (changes in CT values during non-diastolic period of the heart) based on the extracted slope.

In the above example, the output function determining processing illustrated in FIG. 6 is used in the output function obtaining processing, but the present invention is not limited thereto, and processing such as the output function determining processing illustrated in FIG. 6 may be used in the input function obtaining processing. For example, when the input function based on the first TDC is determined, the input function may be determined from the slope as in the output function determining processing. Since such image processing can be analyzed by a simpler method than that for the conventional image processing, the load on the image processing device 100 due to the image processing can also be reduced.

In the above example, in order to image the first CT image, dynamic imaging was performed by the test injection method using the contrast medium diluted with the physiological saline, but the present invention is not limited thereto. For example, the imaging may be performed by a bolus tracking method in which the ROI is set in the target region and the CT value (ROI value) of the ROI is monitored in real time. Dynamic imaging may be performed by the test injection method using the undiluted contrast medium, or dynamic imaging may be performed by a so-called test bolus tracking method in which the test injection method and the bolus tracking method are combined. That is, in the above-described example, in order to optimize the timing of performing imaging for capturing the second CT image, the first CT image can be captured using various techniques.

In the above example, the procedure is such that the first CT image is obtained by the imaging by the test injection method using a diluted contrast medium and then the second CT image is obtained by the imaging using a non-diluted contrast medium, but the present invention is not limited thereto. For example, a method may be such that the second CT image is captured by capturing a plurality of heart phases only at a predetermined heartbeat during execution of the imaging with the test injection method for capturing the first CT image.

In the above-described example, the target pixel extraction unit 131 performs the extraction processing described above, but the present invention is not limited thereto, and the target pixel extraction unit 131 may execute the following processing for pixels. For example, the target pixel extraction unit 131 may select a pixel based on a changed amount of the CT value of each pixel in the time series CT images in a plurality of frames. An example of the changed amount includes a value representing the difference between the maximum value and the minimum value. Specifically, the target pixel extraction unit 131 may obtain the difference between the maximum value and the minimum value of the CT values in all the frame images corresponding to a single slice, and extract a pixel with the difference of a predetermined value (for example, 50 to 150). Furthermore, the target pixel extraction unit 131 may execute such extraction processing in addition to the extraction processing described above, or may execute only one of them.

In the example described above, the upper limit frame Fa is determined by the method described above in the input function determining processing, but the present invention is not limited thereto. For example, the rate of change of the first TDC may be obtained, and any frame between the frame where the rate of change becomes maximum and the frame where the rate of change becomes 0 may be set as the upper limit frame Fa.

In the above example, in the input function determining processing, the function approximation is performed for the first TDC with the two functions corresponding to the straight line and the quadratic curve, but the present invention is not limited to this. For example, the ROI values before the nth frame Fn may be approximated with the straight line L, and the distribution of the ROI values or the CT values at and after the nth frame Fn may be approximated with a straight line or a higher-order function which is third orders or higher. Alternatively, the distribution of the ROI values or the CT values in all the frames up to the upper limit frame Fa may be approximated with a function represented by a multidimensional polynomial. Alternatively, the first TDC may be approximated with three or more functions. For example, the frames from the second frame to the upper limit frame Fa−1 may be divided into three sections or more, and approximation may be performed in each section with a predetermined function. In the first TDC, the ROI value or the CT value might temporarily drop immediately before the curve largely rises (the ROI value or the CT value sharply rises). When this happens, the frames may be divided into: a section (first section) in which the ROI value or the CT value is almost constant and thus approximation with a straight line can be achieved; a section (second section) in which the ROI value or the CT value drops; and a section (third section) in which the ROI value or the CT value sharply rises thereafter. Then, approximation may be performed with the straight line in the first section, a function of second order or higher in the second section, and another function of second order or higher in the third section. In such a case, one of the frame at a boundary between the first and the second sections, and the frame at the boundary between the second and the third sections may be determined as the AT, and the ROI value or the CT value of the frame corresponding to the AT may be determined as the base value.

The first TDC may be approximated with a single function. For example, the first TDC may be approximated with a single function by fitting a normal cumulative distribution function or a cumulative distribution function to the first TDC. When function approximation is performed for the first TDC with the normal cumulative distribution function, a standard deviation (SD) and a mean value of the normal distribution may be selected to achieve best fitting to the rising curve of the first TDC. For example, in this case, the frame closest to −3SD of the normal cumulative distribution function approximated to the first TDC may be determined as the AT and the ROI value or the CT value of the frame corresponding to the AT may be determined as the base value.

In the above-described example, function approximation is performed for the first TDC that is smoothed in the function determining processing, but the present invention is not limited thereto, and the first TDC may be smoothed by a method other than the fitting to the mth-order function described above. For example, the first TDC may be generated with an average value involving peripheral pixels obtained and used to smooth the first TDC, or the first TDC may be smoothened with a moving average. Function approximation may be performed for the first TDC that is not smoothed.

In the example described above, the result of the quantitative analysis performed by the blood flow analysis processing unit 150 is displayed on the display device 170 as described above, but the present invention is not limited thereto. For example, an image appropriately divided into a plurality of segments of a heart region may be displayed on the display device 170, with each segment displayed with a display mode corresponding to the blood flow rate in the segment. Alternatively, a 3D image of an organ based on the image data stored in the image data storage unit 110 may be displayed with each pixel in the 3D image displayed in accordance with the blood flow rate. The CT image may be displayed as a 3D image based on coordinate information on each pixel.

Although the present invention has been described on the basis of examples and modifications, the embodiment of the present invention described above is for the purpose of facilitating the understanding of the present invention, and is not intended to limit the present invention. The present invention can be modified and improved without departing from its spirit and claims, and the present invention includes equivalents thereof.

LIST OF REFERENCE SIGNS 100 image processing device
110 Image data storage unit
120 Input function obtaining unit
121 ROI setting unit
123 Change-over-time determining unit
125 Function approximation processing unit
129 Input function data storage unit
130 Output function obtaining unit
131 Target pixel extraction unit
133 CT change-over-time determining unit
137 Output function approximation processing unit
139 Output function data storage unit
150 Blood flow analysis processing unit
160 Input device
170 Display device

The invention claimed is:

1. A non-transitory computer-readable recording medium storing a computer program for an image processing device including a storage unit that stores therein image data including time-series computed tomography (CT) images in a plurality of frames, of an organ of a subject captured after a contrast medium has been administered, wherein
the storage unit stores
first image data including CT images in a first predetermined number of frames and
second image data including CT images in a second predetermined number of frames that is smaller than the first predetermined number,
the computer program causes the image processing device to execute
a first step of determining a change-over-time of a CT value based on the first image data,
a second step of determining a maximum timing that is a timing at which the CT value becomes a maximum value in a change-over-time of the CT value determined in the first step based on the first image data,
a third step of determining a change-over-time of a CT value based on the second image data including CT images in the second predetermined number of frames based on the maximum timing determined in the second step,
a fourth step of determining a predetermined slope that is a slope of the CT value with respect to a predetermined time based on a change-over-time of the CT value determined in the third step based on the second image data, and
a fifth step of approximating a change-over-time of the CT value with a predetermined function based on the predetermined slope determined in the fourth step based on the second image data.

2. The recording medium storing the computer program according to claim 1, wherein
the predetermined slope is a slope of the CT value with respect to the predetermined time and is larger than a predetermined value.

3. The recording medium storing the computer program according to claim 1, wherein
the second image data includes CT images in the second predetermined number of frames corresponding to one beat of the organ based on the maximum timing determined in the second step.

4. An image processing device comprising:
a storage unit that stores therein first image data including time-series computed tomography (CT) images in a first predetermined number of frames and second image data including CT images in a second predetermined number of frames that is smaller than the first predetermined number, of an organ of a subject captured after a contrast medium has been administered;
a first unit that determines a change-over-time of a CT value based on the first image data;
a second unit that determines a maximum timing that is a timing at which the CT value becomes a maximum value in a change-over-time of the CT value determined in the first unit based on the first image data;
a third unit that determines a change-over-time of a CT value based on the second image data including CT images in the second predetermined number of frames based on the maximum timing determined by the second unit;
a fourth unit that determines a predetermined slope that is a slope of the CT value with respect to a predetermined time based on a change-over-time of the CT value determined by the third unit based on the second image data; and
a fifth unit that approximates a change-over-time of the CT value with a predetermined function based on the predetermined slope determined by the fourth unit based on the second image data.

5. An image processing method that is executed by an image processing device including a storage unit that stores therein image data including time-series computed tomography (CT) images in a plurality of frames, of an organ of a subject captured after a contrast medium has been administered, wherein the storage unit stores first image data including CT images in a first predetermined number of frames and second image data including CT images in a second predetermined number of frames that is smaller than the first predetermined number, and the image processing device executes a first step of determining a change-over-time of a CT value based on the first image data, a second step of determining a maximum timing that is a timing at which the CT value becomes a maximum value in a change-over-time of the CT value determined in the first step based on the first image data, a third step of determining a change-over-time of a CT value based on the second image data including CT images in the second predetermined number of frames based on the maximum timing determined in the second step, a fourth step of determining a predetermined slope that is a slope of the CT value with respect to a predetermined time based on a change-over-time of the CT value determined in the third step based on the second image data, and a fifth step of approximating a change-over-time of the CT value with a predetermined function based on the predetermined slope determined in the fourth step based on the second image data.

* * * * *